(12) United States Patent
Rangwala et al.

(10) Patent No.: US 6,740,488 B2
(45) Date of Patent: May 25, 2004

(54) COTTON EVENT PV-GHGT07(1445) COMPOSITIONS AND METHODS FOR DETECTION THEREOF

(75) Inventors: Tasneem S Rangwala, Chesterfield, MO (US); Minwei Ye, Framingham, MA (US)

(73) Assignee: Monsanto Technology LLC, St. Louis, MO (US)

( * ) Notice: Subject to any disclaimer, the term of this patent is extended or adjusted under 35 U.S.C. 154(b) by 71 days.

(21) Appl. No.: 09/682,769

(22) Filed: Oct. 17, 2001

(65) Prior Publication Data

US 2002/0120964 A1 Aug. 29, 2002

Related U.S. Application Data

(60) Provisional application No. 60/243,190, filed on Oct. 25, 2000.

(51) Int. Cl.$^7$ .............. C12Q 1/68; C12P 19/34; C07H 21/04

(52) U.S. Cl. .............. 435/6; 435/91.2; 536/24.31; 536/24.3

(58) Field of Search ................ 435/6, 91.2; 536/24.31, 536/24.3

(56) References Cited

U.S. PATENT DOCUMENTS 6,462,258 B1 * 10/2002 Fincher et al. .............. 800/300

* cited by examiner

*Primary Examiner*—Ethan Whisenant
*Assistant Examiner*—Joyce Tung
(74) *Attorney, Agent, or Firm*—E. Clifford Lawson; Grace L. Bonner; Dennis R. Hoerner, Jr.

(57) ABSTRACT

The present invention provides DNA compositions and assays for detecting the presence of the DNA compositions in PV-GHGT07(1445) cotton event based on the DNA sequence of the recombinant construct inserted into the cotton genome and of the genomic sequences flanking the insertion site. Kits and conditions useful in conducting the assays are provided.

1 Claim, No Drawings

SEQUENCE LISTING

<160> NUMBER OF SEQ ID NOS: 12

<210> SEQ ID NO 1
<211> LENGTH: 25
<212> TYPE: DNA
<213> ORGANISM: Gossypium hirsutum

<400> SEQUENCE: 1
tgcgatacta ggcttttggt ttctt                                              25

<210> SEQ ID NO 2
<211> LENGTH: 27
<212> TYPE: DNA
<213> ORGANISM: Pisum sativum

<400> SEQUENCE: 2
agttatactc atggatttgt agttgag                                            27

<210> SEQ ID NO 3
<211> LENGTH: 24
<212> TYPE: DNA
<213> ORGANISM: Agrobacterium tumefaciens

<400> SEQUENCE: 3
aggcatcttg aacgatagcc tttc                                               24

<210> SEQ ID NO 4
<211> LENGTH: 26
<212> TYPE: DNA
<213> ORGANISM: Gossypium hirsutum

<400> SEQUENCE: 4
aacacctaat acaagtcata cataca                                             26

<210> SEQ ID NO 5
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: artificial DNA sequence, part cotton genome and part transgene

<400> SEQUENCE: 5
cgattcagat caaacact                                                      18

<210> SEQ ID NO 6
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: artificial DNA sequence, part cotton genome and part transgene

<400> SEQUENCE: 6
caaatgtcaa tagcttgg                                                      18

<210> SEQ ID NO 7
<211> LENGTH: 320
<212> TYPE: DNA
<213> ORGANISM: Artificial Sequence
<220> FEATURE:
<221> NAME/KEY: misc_feature
<222> LOCATION: (1)..(320)
<223> OTHER INFORMATION: artificial DNA sequence, part cotton genome and part transgene

<400> SEQUENCE: 7

```
ttgcgatact aggcttttgg tttctttggt ttatgtgata tttggtatta ttttattcaa      60
atacggtggc taacataagt agctgtgagt gagatgatcc cagtaatgtc taaaatcacg     120
gagcataaac ttaataaata taattatctt gattggagta agacgattca gatcaaacac     180
tgatagttta aactgaaggc gggaaacgac aatctgatcc cagcttgggc tgcaggtcga     240
ttgatgcatg ttgtcaatca attggcaagt cataaaatgc attaaaaaat attttcatac     300
tcaactacaa atccatgagt                                                 320
```

<210> SEQ ID NO 8
<211> LENGTH: 499
<212> TYPE: DNA
<213> ORGANISM: Artificial Sequence
<220> FEATURE:
<221> NAME/KEY: misc_feature
<222> LOCATION: (1)..(499)
<223> OTHER INFORMATION: artificial DNA sequence, part cotton genome and part transgene

<400> SEQUENCE: 8

```
ggcatttgta ggtgccacct tccttttcta ctgtccttt gatgaagtga caggtaggat       60
cggaaagcta gcttggctgc cattttttggg gtgaggccgt tcgcggccga ggggcgccag    120
cccctggggg gatgggaggc ccgcgttagc gggccgggag ggttcgagaa gggggggcac     180
cccccttcgg cgtgcgcggt cacgcgcaca gggcgcagcc ctggttaaaa acaaggttta    240
taaatattgg tttaaaagca ggttaaaaga caggttagcg gtggccgaaa acgggcgga     300
aaccccttgca aatgctggat tttctgcctg tggacagccc ctcaaatgtc aataggtgcg   360
cccctcaaat gtcaatagct tggctgagaa atgatgcatg acttttggag atctaaagct    420
ttattggcag taaggtaatt gccttggcta accactttaa atttgttaaa gaattaattg   480
tttacttgga attttgtat                                                499
```

<210> SEQ ID NO 9
<211> LENGTH: 22
<212> TYPE: DNA
<213> ORGANISM: artificial sequence
<220> FEATURE:
<221> NAME/KEY: misc_feature
<222> LOCATION: (1)..(22)
<223> OTHER INFORMATION: synthetic primer sequence

<400> SEQUENCE: 9

```
gatccatccc atagggtcga tc                                              22
```

<210> SEQ ID NO 10
<211> LENGTH: 24
<212> TYPE: DNA
<213> ORGANISM: artificial sequence
<220> FEATURE:
<221> NAME/KEY: misc_feature
<222> LOCATION: (1)..(24)
<223> OTHER INFORMATION: synthetic primer sequence

<400> SEQUENCE: 10

```
ctaagatcga actctccgac acta                                            24
```

<210> SEQ ID NO 11
<211> LENGTH: 22
<212> TYPE: DNA

```
<213> ORGANISM: artificial sequence
<220> FEATURE:
<221> NAME/KEY: misc_feature
<222> LOCATION: (1)..(22)
<223> OTHER INFORMATION: synthetic primer sequence

<400> SEQUENCE: 11
ccaaggcaat taccttactg cc                                              22

<210> SEQ ID NO 12
<211> LENGTH: 23
<212> TYPE: DNA
<213> ORGANISM: artificial sequence
<220> FEATURE:
<221> NAME/KEY: misc_feature
<222> LOCATION: (1)..(23)
<223> OTHER INFORMATION: synthetic primer sequence

<400> SEQUENCE: 12
ttaaaagaca ggttagcggt ggc                                             23
```

US 6,740,488 B2

COTTON EVENT PV-GHGT07(1445) COMPOSITIONS AND METHODS FOR DETECTION THEREOF

CROSS REFERENCE TO RELATED APPLICATIONS

This application claims the benefit of U.S. Provisional Application No. 60/243,190, filed Oct. 25, 2000, herein incorporated by reference in its entirety.

BACKGROUND OF INVENTION

The present invention relates to the field of plant molecular biology, more specifically the invention relates to transgenic glyphosate tolerance in a plant. The invention more specifically relates to a glyphosate tolerant cotton plant PV-GHGT07(1445) and to assays for detecting the presence of cotton plant PV-GHGT07(1445) DNA in a sample and compositions thereof.

Cotton is an important fiber crop in many areas of the world. The methods of biotechnology have been applied to cotton for improvement of the agronomic traits and the quality of the product. The method of introducing transgenes into cotton plants is demonstrated in U.S. Pat. No. 5,004,863. One such agronomic trait important in cotton production is herbicide tolerance, in particular, tolerance to glyphosate herbicide. This trait has been introduced into cotton plants and is a successful product now used in cotton production. The expression of foreign genes in plants is known to be influenced by their chromosomal position, perhaps due to chromatin structure (e.g., heterochromatin) or the proximity of transcriptional regulation elements (e.g., enhancers) close to the integration site (Weising et al., Ann. Rev. Genet 22:421–477, 1988). For this reason, it is often necessary to screen a large number of events in order to identify an event characterized by optimal expression of a introduced gene of interest. For example, it has been observed in plants and in other organisms that there may be a wide variation in levels of expression of introduced genes among events. There may also be differences in spatial or temporal patterns of expression, for example, differences in the relative expression of a transgene in various plant tissues, that may not correspond to the patterns expected from transcriptional regulatory elements present in the introduced gene construct. For this reason, it is common to produce hundreds to thousands of different events and screen those events for a single event that has desired transgene expression levels and patterns for commercial purposes. An event that has desired levels or patterns of transgene expression is useful for introgressing the transgene into other genetic backgrounds by sexual outcrossing using conventional breeding methods. Progeny of such crosses maintain the transgene expression characteristics of the original transformant. This strategy is used to ensure reliable gene expression in a number of varieties that are well adapted to local growing conditions.

It would be advantageous to be able to detect the presence of a particular event in order to determine whether progeny of a sexual cross contain a transgene of interest. In addition, a method for detecting a particular event would be helpful for complying with regulations requiring the premarket approval and labeling of foods derived from recombinant crop plants, for example. It is possible to detect the presence of a transgene by any well known nucleic acid detection method such as the polymerase chain reaction (PCR) or DNA hybridization using nucleic acid probes. These detection methods generally focus on frequently used genetic elements, such as promoters, terminators, marker genes, etc. As a result, such methods may not be useful for discriminating between different events, particularly those produced using the same DNA construct unless the sequence of chromosomal DNA adjacent to the inserted DNA ("flanking DNA") is known. An event-specific PCR assay is discussed, for example, by Windels et al. (Med. Fac. Landbouww, Univ. Gent 64/5b:459–462, 1999), who identified glyphosate tolerant soybean event 40-3-2 by PCR using a primer set spanning the junction between the insert and flanking DNA, specifically one primer that included sequence from the insert and a second primer that included sequence from flanking DNA.

This invention relates to the glyphosate herbicide tolerant cotton (*Gossypium hirsutum*) plant PV-GHGT07(1445) sold in the U.S.A. and other countries under the name of Roundup Ready® cotton and to the DNA molecules contained in these cotton plants that are useful in detection methods of Roundup Ready® cotton and progeny thereof.

SUMMARY OF INVENTION

According to an aspect of the invention, compositions and methods are provided for detecting the presence of the transgene/genomic insertion region from a cotton plant designated PV-GHGT07(1445) plants and seeds. DNA sequences are provided that comprise at least one transgene/genomic insertion region junction sequence of PV-GHGT07(1445) identified as SEQ ID NO:5 and SEQ ID NO:6, and complements thereof; wherein an insertion region junction sequence spans the junction between heterologous DNA inserted into the genome and the DNA from the cotton cell flanking the insertion site and is diagnostic for the event.

According to another aspect of the invention, DNA sequences that comprise the novel transgene/genomic insertion region, SEQ ID NO:7 are an aspect of this invention. Included are DNA sequences that comprise a sufficient length of polynucleotides of transgene insert sequence and a sufficient length of polynucleotides of cotton genomic sequence from cotton plant PV-GHGT07(1445) of SEQ ID NO:7 that are useful as primer sequences for the production of an amplicon product diagnostic for cotton plant PV-GHGT07(1445).

According to another aspect of the invention, DNA sequences that comprise the novel transgene/genomic insertion region, SEQ ID NO:8 are an aspect of this invention. Included are DNA sequences that comprise a sufficient length of polynucleotides of transgene insert sequence and a sufficient length of polynucleotides of cotton genomic sequence from cotton plant PV-GHGT07(1445) of SEQ ID NO:8 that are useful as primer sequences for the production of an amplicon product diagnostic for cotton plant PV-GHGT07(1445).

According to another aspect of the invention, the DNA sequences that comprise at least 11 or more nucleotides of the transgene portion of the DNA sequence of SEQ ID NO:7 or complements thereof, and a similar length of 5' flanking cotton DNA sequence of SEQ ID NO:7 or complements thereof are useful as DNA primers in DNA amplification methods. The amplicons produced using these primers are diagnostic for cotton event PV-GHGT07(1445). Therefore the invention also includes the amplicons produced by DNA primers homologous or complementary to SEQ ID NO:7.

According to another aspect of the invention, the DNA sequences that comprise a sufficient length of polynucleotides of the transgene portion of the DNA sequence of SEQ ID NO:8 or complements thereof, and a similar length of 5' flanking cotton DNA sequence of SEQ ID NO:8 or complements thereof are useful as DNA primers in DNA amplification methods. The amplicons produced using these primers are diagnostic for cotton event PV-GHGT07(1445). Therefore the invention also includes the amplicons produced by DNA primers homologous or complementary to SEQ ID NO:7.

According to another aspect of the invention, methods of detecting the presence of DNA corresponding to the cotton event PV-GHGT07(1445) event in a sample are provided. Such methods comprise: (a) contacting the sample comprising DNA with a primer set that, when used in a nucleic acid amplification reaction with DNA from cotton event PV-GHGT07(1445), produces an amplicon that is diagnostic for cotton event PV-GHGT07(1445); (b) performing a nucleic acid amplification reaction, thereby producing the amplicon; and (c) detecting the amplicon.

According to another aspect of the invention, methods of detecting the presence of a DNA corresponding to the PV-GHGT07(1445) event in a sample are provided, such methods comprising: (a) contacting the sample comprising DNA with a probe that hybridizes under stringent hybridization conditions with DNA from cotton event PV-GHGT07(1445) and does not hybridize under the stringent hybridization conditions with a control cotton plant (non-PV-GHGT07(1445) DNA); (b) subjecting the sample and probe to stringent hybridization conditions; and (c) detecting hybridization of the probe to the DNA.

According to another aspect of the invention, methods of producing a cotton plant that tolerates application of glyphosate are provided that comprise the steps of: (a) sexually crossing a first parental cotton line comprising the expression cassettes of the present invention, which confers tolerance to application of glyphosate, and a second parental cotton line that lacks the glyphosate tolerance, thereby producing a plurality of progeny plants; and (b) selecting a progeny plant by the use of molecular markers SEQ ID NO:5 and SEQ ID NO:6. Such methods may optionally comprise the further step of back-crossing the progeny plant to the second parental cotton line to producing a true-breeding cotton plant that tolerates application of glyphosate.

According to another aspect of the invention, methods of determining the zygosity of progeny of a cross with PV-GHGT07(1445) are provided. A method that comprises contacting a sample consisting of cotton DNA with a primer set comprising SEQ ID NO:9, SEQ ID NO:11 and SEQ ID NO:12, that when used in a nucleic-acid amplification reaction with genomic DNA from cotton event PV-GHGT07 (1445), produces a first amplicon that is diagnostic for cotton event PV-GHGT07(1445); and performing a nucleic acid amplification reaction, thereby producing the first amplicon; and detecting the first amplicon; and contacting the sample comprising cotton DNA with said primer set, that when used in a nucleic-acid amplification reaction with genomic DNA from cotton plants produces a second amplicon comprising the native cotton genomic DNA homologous to the cotton genomic region of a transgene insertion identified as cotton event PV-GHGT07 (1445); and performing a nucleic acid amplification reaction, thereby producing the second amplicon; and detecting the second amplicon; and comparing the first and second amplicons in a sample, wherein the presence of both amplicons indicates the sample is heterozygous for the transgene insertion. The foregoing and other aspects of the invention will become more apparent from the following detailed description.

DETAILED DESCRIPTION

The following definitions and methods are provided to better define the present invention and to guide those of ordinary skill in the art in the practice of the present invention. Unless otherwise noted, terms are to be understood according to conventional usage by those of ordinary skill in the relevant art. Definitions of common terms in molecular biology may also be found in Rieger et al., *Glossary of Genetics: Classical and Molecular*, 5th edition, Springer-Verlag: New York, 1991; and Lewin, *Genes V*, Oxford University Press: New York, 1994. The nomenclature for DNA bases as set forth at 37 CFR §1.822 is used.

As used herein, the term "cotton" means *Gossypium hirsutum* and includes all plant varieties that can be bred with cotton, including wild cotton species.

As used herein, the term "comprising" means "including but not limited to".

"Glyphosate" refers to N-phosphonomethylglycine and its salts. Glyphosate is the active ingredient of Roundup® herbicide (Monsanto Co.). Treatments with "glyphosate herbicide" refer to treatments with the Roundup®, Roundup Ultra® herbicide or any other herbicide formulation containing glyphosate. For the purposes of the present invention, the term "glyphosate" includes any herbicidally active form of N-phosphonomethylglycine (including any salt thereof) and other forms that result in the production of the glyphosate anion in plants. Treatments with "glyphosate" refer to treatments with the Roundup® or Roundup Ultra® herbicide formulation, unless otherwise stated. Plant transformation and regeneration in tissue culture use glyphosate or salts of glyphosate. Whole plant assays use formulated Roundup® or Roundup Ultra®. Additional formulations with herbicide activity that contain N-phosphonomethylglycine or any of its salts are herein included as a glyphosate herbicide.

A transgenic "event" is produced by transformation of plant cells with heterologous DNA, i.e ., a nucleic acid construct that includes a transgene of interest, regeneration of a population of plants resulting from the insertion of the transgene into the genome of the plant, and selection of a particular plant characterized by insertion into a particular genome location. The term "event" refers to the original transformant and progeny of the transformant that include the heterologous DNA. The term "event" also refers to progeny produced by a sexual outcross between the transformant and another variety that includes the genomic/transgene DNA. Even after repeated back-crossing to a recurrent parent, the inserted transgene DNA and flanking genomic DNA (genomic/transgene DNA) from the transformed parent is present in the progeny of the cross at the same chromosomal location. The term "event" also refers to DNA from the original transformant and progeny thereof comprising the inserted DNA and flanking genomic sequence immediately adjacent to the inserted DNA that would be expected to be transferred to a progeny that receives inserted DNA including the transgene of interest as the result of a sexual cross of one parental line that includes the inserted DNA (e.g., the original transformant and progeny resulting from selfing) and a parental line that does not contain the inserted DNA.

A glyphosate tolerant cotton plant can be bred by first sexually crossing a first parental cotton plant consisting of a cotton plant grown from PV-GHGT07(1445) seed (also referred to as event 1445) that tolerates application of glyphosate herbicide, and a second parental cotton plant that lacks the tolerance to glyphosate herbicide, thereby producing a plurality of first progeny plants; and then selecting a first progeny plant that is tolerant to application of glyphosate herbicide; and selfing the first progeny plant, thereby producing a plurality of second progeny plants; and then selecting from the second progeny plants a glyphosate herbicide tolerant plant. These steps can further include the back-crossing of the first glyphosate tolerant progeny plant or the second glyphosate tolerant progeny plant to the second parental cotton plant or a third parental cotton plant, thereby producing a cotton plant that tolerates the application of glyphosate herbicide. A cotton crop comprising cotton seeds PV-GHGT07(1445) or progeny thereof can be planted in a field and treated with a sufficient amount of glyphosate herbicide to control the weeds without significantly affecting the cotton crop. A sufficient amount of glyphosate herbicide is about 8 ounces/acre or more, 16 ounces/acre or more, 32 ounces/acre or more, or 64 ounces/acre or more. Any glyphosate containing herbicide formulation can be used to control weeds in a cotton crop comprising PV-GHGT07(1445) plants or progeny thereof.

It is also to be understood that two different transgenic plants can also be mated to produce offspring that contain two independently segregating added, exogenous genes. Selfing of appropriate progeny can produce plants that are homozygous for both added, exogenous genes. Back-crossing to a parental plant and out-crossing with a non-transgenic plant are also contemplated, as is vegetative propagation. Descriptions of other breeding methods that are commonly used for different traits and crops can be found in one of several references, e.g., Fehr, in *Breeding Methods for Cultivar Development*, Wilcox J. ed., American Society of Agronomy, Madison Wis. (1987) herein incorporated by reference in its entirety; Poehlman, J. M. (1987); Breeding Field Crops, 3rd ed. Van Nostrand Reinhold, N.Y., Knott, D. R. (1987); herein incorporated by reference in its entirety. Backcross breeding has been used to transfer genes for a simply inherited, highly heritable trait into a desirable homozygous cultivar or inbred line, which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting parent is expected to have the attributes of the recurrent parent (e.g., cultivar) and the desirable trait transferred from the donor parent.

The DNA molecules of the present invention can by used as molecular markers in a marker assisted breeding (MAB) method. DNA molecules of the present invention can be used in methods, such as, AFLP markers, RFLP markers, RAPD markers, SNPs, and SSRs that identify genetically linked agronomically useful traits as described by Walton, *Seed World* 22–29 (July, 1993), the entirety of which is herein incorporated by reference; Burow and Blake, *Molecular Dissection of Complex Traits*, 13–29, Eds. Paterson, CRC Press, New York (1988), the entirety of which is herein incorporated by reference). The glyphosate tolerance trait can be tracked in the progeny of a cross with cotton plant PV-GHGT07 (1445) plants or progeny thereof and any other cotton cultivar or variety using the MAB methods. The DNA molecules are markers for this trait and in MAB methods that are well known in the art can be used to track glyphosate tolerance in cotton where PV-GHGT07 (1445) plants or progeny thereof was a parent or ancestor.

Commercial glyphosate cotton varieties containing genomic/transgene DNA from cotton event PV-GHGT07 (1445) are known as Roundup Ready® cotton and have been introduced and are available in at least the following varieties: Acala Riata RR, DP 409 B/RR, DP 420 RR, DP 422 B/RR, DP 425 RR, DP 429 RR, DP 436 RR, DP 450 B/RR, DP 451 B/RR, DP 458 B/RR, DP5415 RR, DP 5690 RR DP 6100 RR Acala, DP 655 B/RR, DP 90 RR, DP 9834 B.RR, PM 1215 BG/RR, PM 1218 BG/RR, PV 1220 BG/RR, PM 1244 BG/RR, PM 1560 BG/RR, PM 2145 RR, PM 2156 RR, PM 2200 RR, PM 2280 BG/RR, PM 2326 RR, PM 2326 BG/RR, PM 2320 RR, PM 2379 RR, ST 4892 BR, SG 125 BR, SG 125 R, SG 150 BR, SG 150 R, SG 501 BR, SG 521 BR, and SG 521 R. These glyphosate tolerant cotton varieties and any glyphosate tolerant cotton variety derived from these varieties represent the progeny of the cotton event PV-GHGT07(1445). The methods of the present invention can be used to identify any glyphosate tolerant cotton variety that is a progeny of cotton event PV-GHGT07(1445).

A "probe" is an isolated nucleic acid to which is attached a conventional detectable label or reporter molecule, e.g., a radioactive isotope, ligand, chemiluminescent agent, or enzyme. Such a probe is complementary to a strand of a target nucleic acid, in the case of the present invention, to a strand of genomic DNA from cotton event PV-GHGT07 (1445) whether from a cotton plant or from a sample that includes DNA from the event. Probes according to the present invention include not only deoxyribonucleic or ribonucleic acids but also polyamides and other probe materials that bind specifically to a target DNA sequence and can be used to detect the presence of that target DNA sequence.

"Primers" are isolated nucleic acids that are annealed to a complementary target DNA strand by nucleic acid hybridization to form a hybrid between the primer and the target DNA strand, then extended along the target DNA strand by a polymerase, e.g., a DNA polymerase. Primer pairs of the present invention refer to their use for amplification of a target nucleic acid sequence, e.g., by the polymerase chain reaction (PCR) or other conventional nucleic-acid amplification methods.

Probes and primers are generally 8 polynucleotides or more in length, 18 polynucleotides or more, 24 polynucleotides or more, or 30 polynucleotides or more. Such probes and primers hybridize specifically to a target sequence under high stringency hybridization conditions. Preferably, probes and primers according to the present invention have complete sequence similarity with the target sequence, although probes differing from the target sequence and that retain the ability to hybridize to target sequences may be designed by conventional methods.

Methods for preparing and using probes and primers are described, for example, in *Molecular Cloning: A Laboratory Manual*, 2nd ed., vol. 1–3, ed. Sambrook et al., Cold Spring Harbor Laboratory Press, Cold Spring Harbor, N.Y., 1989 (hereinafter, "Sambrook et al., 1989"), herein incorporated by reference in its entirety; *Current Protocols in Molecular Biology*, ed. Ausubel et al., Greene Publishing and Wiley-Interscience, New York, 1992 (with periodic updates) (hereinafter, "Ausubel et al , 1992"), herein incorporated by reference in its entirety; and Innis et al., *PCR Protocols: A Guide to Methods and Applications*, Academic Press: San Diego, 1990, herein incorporated by reference in its entirety. PCR-primer pairs can be derived from a known sequence, for example, by using computer programs intended for that purpose such as Primer (Version 0.5, © 1991, Whitehead Institute for Biomedical Research, Cambridge, Mass.), herein incorporated by reference in its entirety.

Primers and probes based on the flanking DNA and insert sequences disclosed herein can be used to confirm (and, if necessary, to correct) the disclosed sequences by conventional methods, erg., by re-cloning and sequencing such sequences.

The nucleic acid probes and primers of the present invention hybridize under stringent conditions to a target DNA sequence. Any conventional nucleic acid hybridization or amplification method can be used to identify the presence of DNA from a transgenic event in a sample. Nucleic acid molecules or fragments thereof are capable of specifically hybridizing to other nucleic acid molecules under certain circumstances. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., 1989, and by Haymes et al., In: *Nucleic Acid Hybridization, A Practical Approach*, IRL Press, Washington, D.C. (1985), herein incorporated by reference in its entirety. Departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed.

As used herein, a substantially homologous sequence is a nucleic acid sequence that will specifically hybridize to the complement of the nucleic acid sequence to which it is being compared under high stringency conditions. The term "stringent conditions" is functionally defined with regard to the hybridization of a nucleic-acid probe to a target nucleic acid (i.e., to a particular nucleic-acid sequence of interest) by the specific hybridization procedure discussed in Sambrook et al., 1989, at 9.52–9.55. See also, Sambrook et al., 1989 at 9.47–9.52, 9.56–9.58 herein incorporated by reference in its entirety; Kanehisa, (Nucl. Acids Res. 12:203–213, 1984, herein incorporated by reference in its entirety); and Wetmur and Davidson, (J. Mol. Biol. 31:349–370, 1988, herein incorporated by reference in its entirety). Accordingly, the nucleotide sequences of the invention may be used for their ability to selectively form duplex molecules with complementary stretches of DNA fragments. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by about 0.02 M to about 0.15 M NaCl at temperatures of about 50° C. to about 70° C. A stringent conditions, for example, is to wash the hybridization filter at least twice with high-stringency wash buffer (0.2×SSC, 0.1% SDS, 65° C.). Appropriate stringency conditions which promote DNA hybridization, for example, 6.0×sodium chloride/sodium citrate (SSC) at about 45° C., followed by a wash of 2.0×SSC at 50° C., are known to those skilled in the art or can be found in *Current Protocols in Molecular Biology*, John Wiley & Sons, New York (1989), 6.3.1–6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. Such selective conditions tolerate little, if any, mismatch between the probe and the template or target strand. Detection of DNA sequences via hybridization is well-known to those of skill in the art, and the teachings of U.S. Pat. Nos. 4,965,188 and 5,176,995 are exemplary of the methods of hybridization analyses.

In a particularly preferred embodiment, a nucleic acid of the present invention will specifically hybridize to one or more of the nucleic acid molecules set forth in SEQ ID NO:5 and SEQ ID NO:6 or complements or fragments of either under high stringency conditions. In one aspect of the present invention, a marker nucleic acid molecule of the present invention has the nucleic acid sequence set forth in SEQ ID NO:5 or SEQ ID NO:6 or complements thereof or fragments of either.

In another aspect of the present invention, a marker nucleic acid molecule of the present invention shares between 80% and 100% or 90% and 100% sequence identity with the nucleic acid sequence set forth in SEQ ID NO:5 and 6 or complement thereof or fragments of either. In a further aspect of the present invention, a marker nucleic acid molecule of the present invention shares between 95% and 100% sequence identity with the sequence set forth in SEQ ID NO:5 and SEQ ID NO:6 or complement thereof or fragments of either. SEQ ID NO:5 and SEQ ID NO:6 may be used as markers in plant breeding methods to identify the progeny of genetic crosses similar to the methods described for simple sequence repeat DNA marker analysis, in "DNA markers: Protocols, applications, and overviews: (1997) 173–185, Cregan, et al., eds., Wiley-Liss New York; herein incorporated by reference in its entirely. The hybridization of the probe to the target DNA molecule can be detected by any number of methods known to those skilled in the art, these can include, but are not limited to, fluorescent tags, radioactive tags, antibody based tags, and chemiluminescent tags.

Regarding the amplification of a target nucleic acid sequence (e.g., by PCR) using a particular amplification primer pair, "stringent conditions" are conditions that permit the primer pair to hybridize only to the target nucleic-acid sequence to which a primer having the corresponding wild-type sequence (or its complement) would bind and preferably to produce a unique amplification product, the amplicon.

The term "specific for (a target sequence)" indicates that a probe or primer hybridizes under stringent hybridization conditions only to the target sequence in a sample comprising the target sequence.

As used herein, "amplified DNA" or "amplicon" refers to the product of nucleic-acid amplification of a target nucleic acid sequence that is part of a nucleic acid template. For example, to determine whether the cotton plant resulting from a sexual cross contains transgenic event genomic DNA from the cotton plant of the present invention, DNA extracted from a cotton plant tissue sample may be subjected to nucleic acid amplification method using a primer pair that includes a primer derived from flanking sequence in the genome of the plant adjacent to the insertion site of inserted heterologous DNA, and a second primer derived from the inserted heterologous DNA to produce an amplicon that is diagnostic for the presence of the event DNA. The amplicon is of a length and has a sequence that is also diagnostic for the event. The amplicon may range in length from the combined length of the primer pairs plus one nucleotide base pair, preferably plus about fifty nucleotide base pairs, more preferably plus about two hundred nucleotide base pairs, more preferably plus about three hundred nucleotide base pairs, and even more preferably plus about five hundred nucleotide base pairs. Alternatively, a primer pair can be derived from flanking sequence on both sides of the inserted DNA so as to produce an amplicon that includes the entire insert nucleotide sequence. A member of a primer pair derived from the plant genomic sequence may be located a distance from the inserted DNA sequence, this distance can range from one nucleotide base pair up to about twenty thousand nucleotide base pairs. The use of the term "amplicon" specifically excludes primer dimers that may be formed in the DNA thermal amplification reaction.

Nucleic-acid amplification can be accomplished by any of the various nucleic-acid amplification methods known in the art, including the polymerase chain reaction (PCR). A variety of amplification methods are known in the art and are described, inter alia, in U.S. Pat. No. 4,683,1 95, herein incorporated by reference in its entirety and in U.S. Pat. No. 4,683,202, herein incorporated by reference in its entirety, and in *PCR Protocols: A Guide to Methods and Applications*, ed. Innis et al., Academic Press, San Diego, 1990. PCR amplification methods have been developed to amplify up to 22 kb of genomic DNA and up to 42 kb of bacteriophage DNA (Cheng et al., Proc. Natl. Acad. Sci. USA 91:5695–5699, 1994, herein incorporated by reference in its entirety). These methods as well as other methods known in the art of DNA amplification may be used in the practice of the present invention. The sequence of the heterologous transgene DNA insert or flanking genomic sequence from cotton event PV-GHGT07(1445) can be verified (and corrected if necessary) by amplifying such sequences from the event using primers derived from the sequences provided herein followed by standard DNA sequencing of the PCR amplicon or of the cloned DNA.

The amplicon produced by these methods may be detected by a plurality of techniques. Agarose gel electrophoresis and staining with ethidium bromide is a common well known method of detecting DNA amplicons. Another such method is Genetic Bit Analysis (Nikiforov, et al. Nucleic Acid Res. 22:4167–4175, 1994) where an DNA oligonucleotide is designed which overlaps both the adjacent flanking genomic DNA sequence and the inserted DNA sequence. The oligonucleotide is immobilized in wells of a microwell plate. Following PCR of the region of interest (using one primer in the inserted sequence and one in the adjacent flanking genomic sequence), a single-stranded PCR product can be hybridized to the immobilized oligonucleotide and serve as a template for a single base extension reaction using a DNA polymerase and labelled ddNTPs specific for the expected next base. Readout may be fluorescent or ELISA-based. A signal indicates presence of the insert/flanking sequence due to successful amplification, hybridization, and single base extension.

Another method is the Pyrosequencing technique as described by Winge (Innov. Pharma. Tech. 00:18–24, 2000). In this method an oligonucleotide is designed that overlaps the adjacent genomic DNA and insert DNA junction. The oligonucleotide is hybridized to single-stranded PCR product from the region of interest (one primer in the inserted sequence and one in the flanking genomic sequence) and incubated in the presence of a DNA polymerase, ATP, sulfurylase, luciferase, apyrase, adenosine 5" phosphosulfate and luciferin. DNTPs are added individually and the incorporation results in a light signal which is measured. A light signal indicates the presence of the transgene insert/flanking sequence due to successful amplification, hybridization, and single or multi-base extension.

Fluorescence Polarization as described by Chen et al., (Genome Res. 9:492–498, 1999) is a method that can be used to detect the amplicon of the present invention. Using this method an oligonucleotide is designed which overlaps the genomic flanking and inserted DNA junction. The oligonucleotide is hybridized to single-stranded PCR product from the region of interest (one primer in the inserted DNA and one in the flanking genomic DNA sequence) and incubated in the presence of a DNA polymerase and a fluorescent-labeled ddNTP. Single base extension results in incorporation of the ddNTP. Incorporation can be measured as a change in polarization using a fluorometer. A change in polarization indicates the presence of the transgene insert/flanking sequence due to successful amplification, hybridization, and single base extension.

Taqman® (PE Applied Biosystems, Foster City, Calif.) is described as a method of detecting and quantifying the presence of a DNA sequence and is fully understood in the instructions provided by the manufacturer. Briefly, a FRET oligonucleotide probe is designed which overlaps the genomic flanking and insert DNA junction. The FRET probe and PCR primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking/transgene insert sequence due to successful amplification and hybridization.

Molecular Beacons have been described for use in sequence detection as described in Tyangi et al. (Nature Biotech. 14:303–308, 1996) Briefly, a FRET oligonucleotide probe is designed that overlaps the flanking genomic and insert DNA junction. The unique structure of the FRET probe results in it containing secondary structure that keeps the fluorescent and quenching moieties in close proximity. The FRET probe and PCR primers (one primer in the insert DNA sequence and one in the flanking genomic sequence) are cycled in the presence of a thermostable polymerase and dNTPs. Following successful PCR amplification, hybridization of the FRET probe to the target sequence results in the removal of the probe secondary structure and spatial separation of the fluorescent and quenching moieties. A fluorescent signal results. A fluorescent signal indicates the presence of the flanking genomic/transgene insert sequence due to successful amplification and hybridization.

DNA detection kits can be developed using the compositions disclosed herein and the methods well known in the art of DNA detection. The kits are useful for identification of cotton event PV-GHGT07(1445) DNA in a sample and can be applied to methods for breeding cotton plants containing PV-GHGT07(1445) DNA. The kits contain DNA sequences homologous or complementary to SEQ ID NO:7 or SEQ ID NO:8 or to DNA sequences homologous or complementary to DNA contained in the transgene genetic elements of PV-GHGT07(1445) DNA, these DNA sequences can be used in DNA amplification reactions or as probes in a DNA hybridization method. The kits may also contain the reagents and materials necessary for the performance of the detection method.

The transgene genetic element DNA molecules contained in PV-GHGT07(1445) consists of the cauliflower mosaic virus 35S promoter (P-CaMV.35S, U.S. Pat. No. 5,352,605), herein incorporated by reference in its entirety; operably connected to the neomycin phosphotransferase gene (nptII) (Fraley et al. Proc Natl. Acad Sci USA 80:4803–4807, 1983, herein incorporated by reference in its entirety); operably connected to the nopaline synthase 3" termination region (Fraley et al. Proc Natl. Acad Sci USA 80:4803–4807, 1983, herein incorporated by reference in its entirety); the Figwort mosaic promoter (U.S. Pat. No. 5,378,619, herein incorporated by reference in its entirety); operably connected to an Arabidopsis EPSPS chloroplast transit peptide (TS-At.EPSPS:CTP2, Klee et al., Mol. Gen. Genet. 210:47–442, 1987, herein incorporated by reference in its entirety); operably connected to a glyphosate tolerant 5-enolpyruvylshikimate-3-phosphate synthase (EPSPS) from Agrobacterium sp. strain CP4 (AGRTU.aroA:CP4 EPSPS, U.S. Pat. No. 5,633,435, herein incorporated by reference in its entirety); operably connected to the 3" termination region from pea ribulose 1,5-bisphosphate carboxylase E9 (Coruzzi, et al., EMBO J. 3:1671–1679, herein incorporated by reference in its entirety). The DNA polynucleotide sequences or fragments thereof disclosed in these references can be used as DNA primers or probes in the methods of the present invention.

The following examples are included to demonstrate examples of certain preferred embodiments of the invention. It should be appreciated by those of skill in the art that the techniques disclosed in the examples that follow represent approaches the inventors have found function well in the practice of the invention, and thus can be considered to constitute examples of preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLES

Example 1

DNA from PV-GHGT07(1445) Roundup Ready® cotton event was extracted from cotton leaves containing the PV-GHGT07(1445) event and nontransgenic cotton line Coker 312. Young leaves were ground in liquid nitrogen and the total DNA extracted following a method modified from Fulton et al. Pl. Mol. Biol. Rep. 13:207–209, 1995, herein incorporated by reference in its entirety. Approximately 1 gram of the ground leaf tissue was transferred to 13 milliliters (ml) centrifuge tube containing 6 ml of the extraction buffer [2.5 ml DNA extraction buffer (350 mM Sorbitol, 100 mM Tris pH 7.5, 5 mM EDTA), 2.5 ml nuclei lysis buffer (200 mM Tris pH 7.5, 50 mM EDTA, 2 M NaCl, 2% CTAB), and 1 ml Sarkosyl (5% solution)]. The samples were incubated at 65° C. for approximately 30 minutes with intermittent mixing. Four and a half milliliters of a mixture of chloroform:isoamyl alcohol (24:1) was added to the samples. The suspension was mixed for 2 to 3 minutes, and the two phases separated by centrifugation for 15 minutes at ~2700 rpm at 4° C. The aqueous (top) layer was removed using a transfer pipette and placed into a 13 ml centrifuge tube. Five milliliters of 100% isopropanol were added, and the tubes were mixed by inversion to precipitate the DNA. The precipitated DNA was pelleted by centrifuging at ~2700 rpm for 5 minutes at 4° C. The pellet was washed with approximately 1 ml of 70% ethanol and centrifuged for an additional 5 minutes at ~2700 rpm at 4° C. The DNA was resuspended in 0.25–0.5 ml TE, pH 8.0, and stored in a 4° C. refrigerator.

The DNA extracted from the cotton leaf tissue was used in a PCR DNA amplification of the 5' genomic/transgene insert sequences using primer 1 (SEQ ID NO:1, 5' TGC-GATACTAGGCTTTTGGTTTCTT 3') and primer 2 (SEQ ID NO:2, 5' AGTTATACTCATGGATTTGTAGTTGAG 3'), and the 3' genomic/transgene insert sequences flanking using primer 3 (SEQ ID NO:3, 5' AGGCATCTTGAAC-GATAGCCTTTC 3') and primer 4 (SEQ ID NO:4, 5' AACACCTAATACAAGTCATACATACA 3'). The PCR DNA amplification analyses were conducted using genomic DNA extracted from cotton event PV-GHGT07 (1445) and non-transgenic cotton line Coker 312. The amplification reaction for the 5' flanking genomic sequence was conducted using Supermix from Gibco BRL (Gaithersburg, Md.) with a final concentration of 0.4 µM for Primer 1 and Primer 2 in a 50 µl reaction volume. The PCR for the 3' flanking genomic sequence was conducted in a 50 µl reaction volume containing a final concentration of 1.5 mM $Mg^{2+}$, 200µM each dNTP, 2 units of Taq DNA polymerase, and 0.4 µM of Primer 3 and Primer 4. The reactions were performed under the following cycling conditions: 1 cycle at 94° C. for 1 minute; 30 cycles of 96° C. for 30 seconds, 50° C. for 30 seconds, 72° C. for 45 seconds; 1 cycle at 72° C. for 5 minutes. The PCR products were separated using 2.0% agarose gel electrophoresis at 100 V for ~1 hour and visualized by ethidium bromide staining. PCR products of the expected sizes representing the 5' and 3' flanking sequences were isolated by separation of the PCR products on a 2.0% agarose gel by electrophoresis. PCR products, representing 5' regions that span the junction between the PV-GHGT07(1445) transgenic insertion and the neighboring flanking cotton genomic DNA sequence were purified by agarose gel electrophoresis followed by isolation from the agarose matrix using the QIAquick Gel Extraction Kit (catalog # 28704, Qiagen Inc., Valencia, Calif.). The purified PCR products were then sequenced with by DNA sequence analysis (ABI Prism™ 377, PE Biosystems, Foster City, Calif. and DNASTAR sequence analysis software, DNASTAR Inc., Madison, Wis.).

A portion of the 5' PCR product DNA sequence was determined, resulting in a 320 nucleotide base pair sequence representing the 5' genomic/transgene insert sequence of cotton PV-GHGT07(1445) and identified as SEQ ID NO:7. A portion of the 3' PCR product DNA sequence was determined resulting in a 499 nucleotide base pair sequence representing the 3' genomic/transgene insert sequence of cotton PV-GHGT07(1445) and identified in SEQ ID NO:8.

The genomic/transgene junction sequences, SEQ ID NO:5 and SEQ ID NO:6 are novel DNA sequences in PV-GHGT07(1445) that are diagnostic for cotton plant PV-GHGT07 (1445) and its progeny. SEQ ID NO:5 and SEQ ID NO:6 represent 9 nucleotides on each side of an insertion site of a transgene sequence fragment and the cotton genome. Junction sequence SEQ ID NO:5 is found at nucleotide positions 164–181 of SEQ ID NO:7, and junction sequence SEQ ID NO:6, is located at nucleotide positions 366–383 of SEQ ID NO:8, representing the genomic/transgene junction sequences of the transgene insert with cotton genomic DNA sequence.

Example 2

DNA event primer pairs are used to produce an amplicon diagnostic for PV-GHGT07(1445). These event primer pairs include, but are not limited to SEQ ID NO:9 and SEQ ID NO:10 that when used in a DNA amplification method (PCR) produce an amplicon of about 1107 nucleotide base pairs (bp). In addition to these primer pairs, any primer pair derived from the amplicon product of SEQ ID NO:9 and SEQ ID NO:10, or SEQ ID NO:7, or SEQ ID NO:8 that in a DNA amplification reaction produces an amplicon diagnostic for event 1445 is an aspect of the present invention. The amplification conditions for this analysis are illustrated in Table 1 and Table 2, however, any modification of these methods that use DNA primers to produce an amplicon diagnostic for PV-GHGT07(1445) is within the ordinary skill of the art. The analysis of PV-GHGT07(1445) plant tissue sample should include a positive tissue control from PV-GHGT07(1445), a negative control from a cotton plant that is not PV-GHGT07(1445), and a negative control that contains no template cotton DNA. Additional primer sequences can be selected from SEQ ID NO:7 and SEQ ID NO:8 by those skilled in the art of DNA amplification methods, and conditions optimized for the production of an amplicon that may differ from the methods shown in Table 1 and Table 2, but result in an amplicon diagnostic for PV-GHGT07(1445). The use of these DNA primer sequences with modifications to the methods of Table 1 and 2 are within the scope of the invention. The amplicon produced by the use at least one primer sequence derived from SEQ ID NO:7 and SEQ ID NO:8 that is diagnostic for PV-GHGT07(1445) can be used in the described methods and is an aspect of the invention. The assay for the PV-GHGT07(1445) amplicon can be performed by using a Stratagene Robocycler, MJ Engine, Perkin-Elmer 9700, or Eppendorf Mastercycler Gradient thermocycler as shown in Table 2, or by methods and apparatus known to those skilled in the art.

TABLE 1

PCR procedure and reaction mixture for the confirmation of 1445 5' transgene insert/genomic junction region.

| Step | Reagent | Amount | Comments |
| --- | --- | --- | --- |
| 1 | Nuclease-free water | add to final volume of 50 μl | |
| 2 | 10X reaction buffer (with MgCl$_2$) | 5.0 μl | 1X final concentration of buffer, 1.5 mM final concentration of MgCl$_2$ |
| 3 | 10 mM solution of dATP, dCTP, dGTP, and dTTP | 1 μl | 0.2 μM final concentration of each dNTP |
| 4 | event primer 9 (SEQ ID NO. 9) (resuspended in 1X TE buffer of nuclease-free water to a concentration of 10 μM) | 1 μl | 0.2 μM final concentration |
| 5 | event primer 10 (SEQ ID NO. 10) (resuspended in 1X TE buffer or nuclease-free water to a concentration of 10 μM) | 1 μl | 0.2 μM final concentration |
| 6 | REDTaq DNA polymerase (1 unit/μl) | 0.5 μl (recommended to switch pipets prior to next step) | 1 unit/reaction |
| 8 | Extracted DNA (template) Samples to be analyzed individual leaves pooled leaves | 50–200 ng of genomic DNA | |
| | Negative control | 200 ng of genomic DNA 100 ng of cotton genomic DNA (not 1445) | |
| | Negative control | no DNA template solution | |
| | Positive control | 50–200 ng of 1445 genomic DNA | |

TABLE 2

Suggested PCR parameters for different thermocyclers
Gently mix and, if needed(no hot top hermocycler), add 1–2 drops of mineral oil on top of each reaction. Proceed with the PCR in a Stratagene Robocycler, MJ Engine, Perkin-Elmer 9700 or Eppendorf Mastercycler Gradient thermocycler using the following cycling parameters. The MJ Engine or Eppendorf Mastercycler Gradient themocycler should be run in the calculated mode. Run the Perkin-Elmer 9700 thermocycler with the ramp speed set at maximum

| Cycle No. | Settings: | Stratagene Robocycler |
| --- | --- | --- |
| 1 | 94° C. | 3 minutes |
| 30 | 96° C. | 1 minute |
| | 60° C. | 1 minute |
| | 72° C. | 1 minute |
| 1 | 72° C. | 5 minutes |

| Cycle No. | Settings: | MJ Engine or Perkin-Elmer 9700 |
| --- | --- | --- |
| 1 | 94° C. | 4 minutes |
| 40 | 94° C. | 1 minute |
| | 64° C. | 30 seconds |
| | 68° C. | 3 minute |
| 1 | 72° C. | 5 minutes |

TABLE 2-continued

Suggested PCR parameters for different thermocyclers
Gently mix and, if needed(no hot top hermocycler), add 1–2 drops
of mineral oil on top of each reaction. Proceed with the
PCR in a Strategene Robocycler, MJ Engine, Perkin-Elmer 9700 or
Eppendorf Mastercycler Gradient thermocycler using the
following cycling parameters. The MJ Engine or Eppendorf Mastercycler
Gradient themocycler should be run in the calculated mode. Run
the Perkin-Elmer 9700 thermocycler with the ramp speed set at maximum

| Cycle No. | Settings: | Eppendorf Mastercycler Gradient |
|---|---|---|
| 1 | 94° C. | 3 minutes |
| 30 | 96° C. | 15 seconds |
|  | 60° C. | 15 seconds |
|  | 72° C. | 1 minute |
| 1 | 72° C. | 5 minutes |

Example 3

The methods used to identify heterozygous from homozygous cotton progeny containing event PV-GHGT07(1445) are described in the zygosity assay in Table 3 and Table 4. The DNA primers used in the zygosity assay are primer 9, 5'-GATCCATCCCATAGGGTCGATC 3' (SEQ ID NO:9), primer 11, 5' CCAAGGCAATTACCTTACTGCC 3' (SEQ ID NO:11), and primer 12, 5' TTAAAAGACAGGTTAGCGGTGGC 3' (SEQ ID NO:12).

SEQ ID NO:9, SEQ ID NO:11 and SEQ ID NO:12 when used in these reaction methods produce a DNA amplicon of about 455 bp for non-transgenic cotton, two DNA amplicons of about 455 bp and about 184 bp for heterozygous cotton containing event PV-GHGT07(1445), and a DNA ampilicon of about 184 bp for homozygous cotton containing event PV-GHGT07 (1445). The controls for this analysis should include a positive control from homozygous and heterozygous cotton containing event PV-GHGT07(1445), a negative control from non-transgenic cotton, and a negative control that contains no template DNA. This assay is optimized for use with a Stratagene Robocycler, MJ Engine, Perkin-Elmer 9700, or Eppendorf Mastercycler Gradient thermocycler. Other methods and apparatus known to those skilled in the art that produce amplicons that identify the zygosity of the progeny of crosses made with PV-GHGT07 (1445) event cotton plants is within the skill of the art.

TABLE 3

Zygosity assay reaction solutions

| Step | Reagent | Amount | Comments |
|---|---|---|---|
| 1 | Nuclease-free water | add to 20 μl final volume |  |
| 2 | 10X reaction buffer (with MgCl₂) | 2 μl | 1.5 mM final concentration of MgCl₂ |
| 3 | 10 mM solution of dATP, dCTP, dGTP, and dTTP | 0.4 μl | 200 μM final concentration of each dNTP |
| 4 | Primer 9 (resuspended in 1X TE buffer or nuclease-free water to a concentration of 10 μM) | 0.5 μl | 0.25 μM final concentration |
| 5 | Primer 11 (resuspended in 1X TE buffer or nuclease-free water to a concentration of 10 μM) | 0.8 μl | 0.4 μM final concentration |
| 6 | Primer 12 (resuspended in 1X TE buffer or nuclease-free water to a concentration of 10 μM) | 0.3 μl | 0.15 μl final concentration |
| 7 | REDTaq DNA polymerase (1 unit/μl) | 1.0 μl (recommended to switch pipets prior to next step). | 1 unit/reaction |
| 8 | Extracted DNA (template) |  |  |
|  | Samples tube analyzed (individual leases) | 4–80 ng of genomic DNA |  |
|  | Negative control | 4 ng of non-transgenic cotton genomic DNA |  |
|  | Negative control | no DNA template (solution in which DNA was resuspended) |  |
|  | Positive control | 4 ng of genomic DNA from known event 1445 heterozygous cotton |  |
|  | Positive control | 4 ng of genomic DNA from known event 1445 homozygous cotton |  |

TABLE 4

Zygosity assay thermocycler conditions
Gently mix and, if needed(no hot top hermocycler), add 1–2 drops
of mineral oil on top of each reaction. Proceed with the
PCR in a Strategene Robocycler, MJ Engine, Perkin-Elmer 9700 or
Eppendorf Mastercycler Gradient thermocycler using the
following cycling parameters. When running the PCR in the Eppendorf
Mastercycle Gradient or MJ Engine, the thermocycler should be run
in the calculated mode. When ruling the PCR in the Perkin-Elmer 9700,
run the thermocycler with the ramp speed set at maximum.

| Cycle No. | Settings | Stratagene Robocycler |
|---|---|---|
| 1 | 94° C. | 3 minutes |
| 38 | 94° C. | 1 minute |
|  | 60° C. | 1 minute |
|  | 72° C. | 1 minute and 30 seconds |
| 1 | 72° C. | 10 minutes |

| Cycle No. | Settings | MJ Engine or Perkin-Elmer 9700 |
|---|---|---|
| 1 | 94° C. | 3 minutes |
| 38 | 94° C. | 30 seconds |
|  | 60° C. | 30 seconds |
|  | 72° C. | 1 minute and 30 seconds |
| 1 | 72° C. | 10 minutes |

| Cycle No. | Settings | Eppendorf Mastercycler Gradient |
|---|---|---|
| 1 | 94° C. | 3 minutes |
| 38 | 94° C. | 15 seconds |
|  | 60° C. | 15 seconds |
|  | 72° C. | 1 minute and 30 seconds |
| 1 | 72° C. | 10 minutes |

Having illustrated and described the principles of the present invention, it should be apparent to persons skilled in the art that the invention can be modified in arrangement and detail without departing from such principles. We claim all modifications that are within the spirit and scope of the appended claims.

All publications and published patent documents cited in this specification are incorporated herein by reference to the same extent as if each individual publication or patent application was specifically and individually indicated to be incorporated by reference.

What is claimed is:

1. A method of detecting the presence of PV-GHGT07 (1445) cotton event in a sample comprising cotton DNA, the method comprising:
   (a) contacting the sample with a polynucleotide probe having the sequence of SEQ ID NO:5 or SEQ ID NO:6;
   (b) subjecting the sample and said probe to stringent hybridization conditions; and
   (c) detecting hybridization of the probe to the DNA.

* * * * *